US009619997B2

(12) United States Patent
Treacy et al.

(10) Patent No.: US 9,619,997 B2
(45) Date of Patent: Apr. 11, 2017

(54) SYSTEM AND METHOD FOR PHYSIOLOGICAL MONITORING

(71) Applicant: GENERAL ELECTRIC COMPANY, Schenectady, NY (US)

(72) Inventors: Stephen Thomas Treacy, Menomonee Falls, WI (US); Michael John Palmer, New Berlin, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 10 days.

(21) Appl. No.: 14/564,280

(22) Filed: Dec. 9, 2014

(65) Prior Publication Data

US 2016/0163187 A1    Jun. 9, 2016

(51) Int. Cl.
*G08B 29/26* (2006.01)
*A61B 5/00* (2006.01)
*G08B 21/06* (2006.01)
*G08B 21/04* (2006.01)

(52) U.S. Cl.
CPC .............. *G08B 29/26* (2013.01); *A61B 5/746* (2013.01); *G08B 21/04* (2013.01)

(58) Field of Classification Search
None
See application file for complete search history.

(56) References Cited

U.S. PATENT DOCUMENTS 8,665,096 B2    3/2014 Rantala et al.
2011/0270058 A1*   11/2011 Price .................... A61B 5/021
                                                           600/324

* cited by examiner

*Primary Examiner* — Daniell L Negron
(74) *Attorney, Agent, or Firm* — Grogan, Tuccillo & Vanderleeden, LLP

(57) ABSTRACT

A method of adjusting event detection and alarm generation sensitivity settings of a patient monitoring system includes receiving physiological information from a patient, determining an acuity level of the patient in dependence upon the physiological information received, and at least one of automatically updating a sensitivity setting for a system action in dependence upon the determined acuity level of the patient or prompting a user to manually update the sensitivity setting for the system action in dependence upon the determined acuity level.

23 Claims, 3 Drawing Sheets

SYSTEM AND METHOD FOR PHYSIOLOGICAL MONITORING

BACKGROUND

Technical Field

Embodiments of the invention relate generally to patient monitoring and, more specifically, to a system and method of automatically adjusting event detection and alarm generation sensitivity settings of a patient monitoring system.

Discussion of Art

Patient monitoring systems include electronic monitoring devices designed to display physiological information about a patient. Electrocardiogram (ECG), electroencephalogram (EEG), plethysmographic signals, and signals related to blood pressure, temperature, and respiration represent typical physiological information contained in monitoring devices. Patient monitoring systems are typically also furnished with alarming functionality to alert clinicians of important physiological events that may impact a patient being monitored. Such systems maintain alarm configuration settings that are used to determine when an alarm event is triggered by the devices.

As will be readily appreciated, the sensitivity of the event detection and alarm generation mechanism is a key attribute of patient monitoring systems because insufficient sensitivity can result in missed events, and overly sensitive systems can lead to alarm fatigue. Alarm fatigue is the condition in which clinicians at medical institutions become desensitized to clinical alarms because of the high probability that the alarms are not of actual clinical significance. Most event detection systems, therefore, provide a sensitivity setting to allow clinical users to tune the detection in a way that gives the desired clinical performance for each patient. For example, the alarm configuration settings typically include threshold limits and priority levels that can be customized by the clinicians or caregivers based on the acuity of the patient and monitoring needs. Clinicians typically desire more sensitive event detection when dealing with acute patients, and they are willing to reduce the sensitivity in favor of fewer alarms for patients who are less acute. However, clinicians may sometimes ignore these manually adjustable sensitivity controls and instead rely on the default settings, or forget to adjust the sensitivity controls on a periodic basis as the patient's condition changes; therefore, existing systems may not perform as well as they could.

In view of the above, it is desirable to provide a system and related method that is configured to automatically prompt a user to adjust, or to automatically adjust, the event detection and alarm generation sensitivity settings of a patient monitoring system.

BRIEF DESCRIPTION

In an embodiment, a method of adjusting event detection and alarm generation sensitivity settings of a patient monitoring system is provided. The method includes the steps of receiving physiological information from a patient, determining an acuity level of the patient in dependence upon the physiological information received, and at least one of automatically updating a sensitivity setting for a system action in dependence upon the determined acuity level of the patient or prompting a user to manually update the sensitivity setting for the system action in dependence upon the determined acuity level.

In an embodiment, a method of physiological monitoring utilizing a patient monitoring system is provided. The method includes the steps of determining an acuity level of a patient in dependence upon physiological information of the patient, and automatically adjusting one of an event detection sensitivity level and an alarm generation sensitivity level of the patient monitoring system in dependence upon the determined acuity level of the patient.

In an embodiment, a system for monitoring a patient is provided. The system includes at least one device connected to the patient and configured to obtain physiological information from the patient, and a control unit electrically connected to the at least one device. The control unit is configured to determine an acuity level of the patient in dependence upon the physiological information and to automatically adjust one of an event detection sensitivity level and an alarm generation sensitivity level in dependence upon the determined acuity level of the patient.

DRAWINGS

The present invention will be better understood from reading the following description of non-limiting embodiments, with reference to the attached drawings, wherein below:

DETAILED DESCRIPTION

Figure 1:
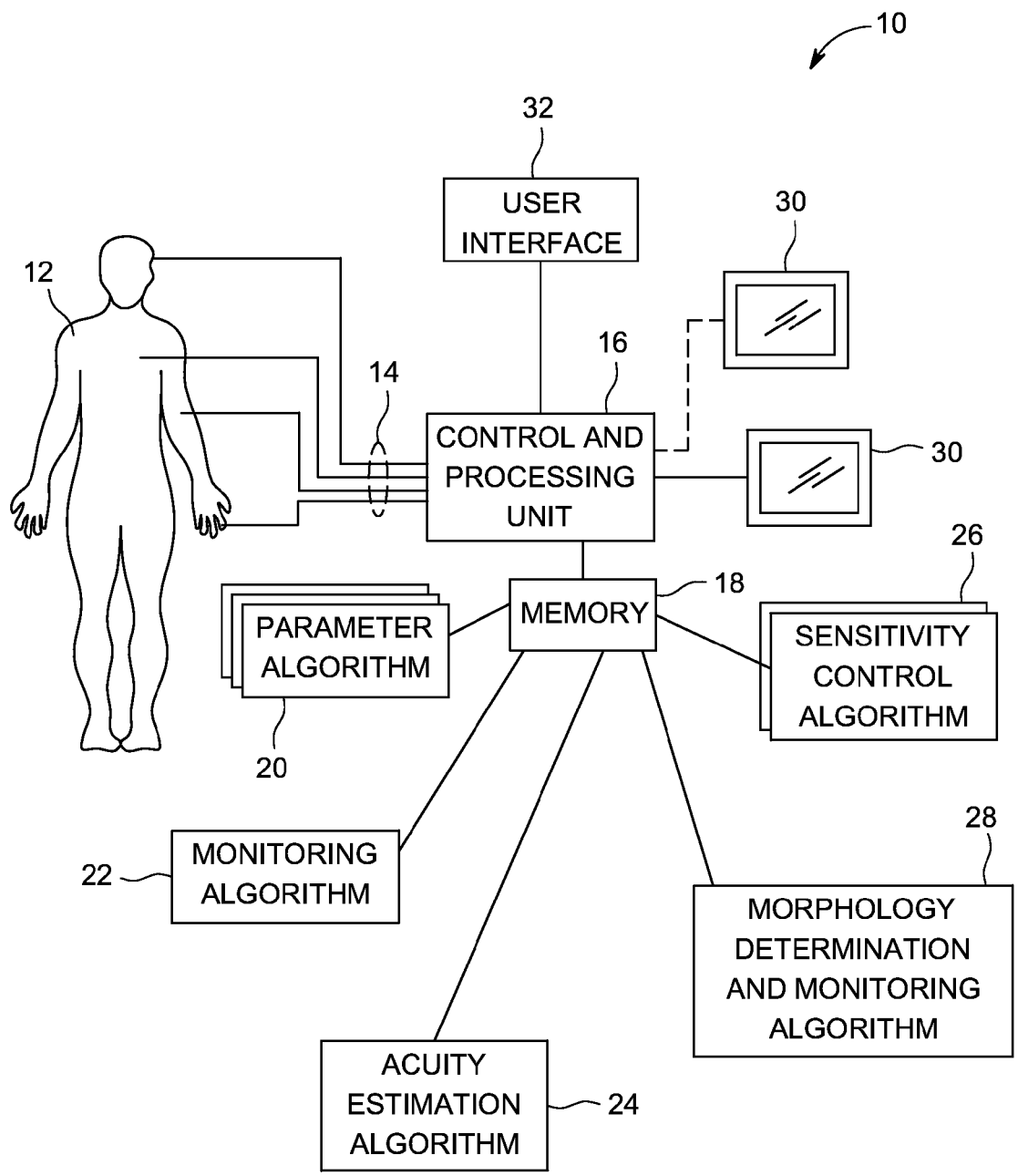
FIG. 1 is a schematic illustration of a system for physiological monitoring of a patient according to an embodiment of the present invention.

Reference will be made below in detail to exemplary embodiments of the invention, examples of which are illustrated in the accompanying drawings. Wherever possible, the same reference characters used throughout the drawings refer to the same or like parts. As used herein, "electrical contact," "electrical communication" and "electrically coupled" means that the referenced elements are directly or indirectly connected such that an electrical current may flow from one to the other. The connection may include a direct conductive connection (i.e., without an intervening capacitive, inductive or active element), an inductive connection, a capacitive connection, and/or any other suitable electrical connection. Intervening components may be present. As used herein, "automatic" or "automatically" means without manual intervention, control or influence from a clinical user. While embodiments of the present invention are described in connection with a patient monitoring system that is configured to adjust event detection and alarm generation sensitivity settings in dependence upon a determined acuity level of a patient, the system is not so limited in this regard. In particular, the system may be equally applicable to the monitoring of a subject, more generally. As used herein, "subject" means a person, animal or other entity that is capable of providing feedback regarding bodily or other parameters of such person, animal or entity. Moreover, the system may be configured to determine any condition of such person, animal or entity including, but not limited to, an acuity level of such person, animal or entity, and to adjust the event detection and alarm generation sensitivity setting in dependence upon any such determined condition. As also used herein, "acuity level" means the level of sickness or the level of severity of an illness or condition.

Referring now to FIG. 1, a patient monitoring system 10 for monitoring a subject or patient 12 is illustrated. As will be readily appreciated, the monitoring system 10 normally acquires a plurality of physiological channel signals 14 from the patient 12 via sensors (not shown), where one physiological channel signal corresponds to one measurement channel. The channel signals 14 typically comprise several types of signals, such as ECG, EEG, EMG, blood pressure, respiration, pulse, temperature and plethysmographic signals.

Based on the raw real-time physiological signal data obtained from the subject 14, a plurality of physiological parameters may be derived, each physiological parameter being calculated from the waveform data of one or more of the physiological channel signals acquired from the subject. The physiological parameter may represent a waveform signal value determined over a predefined period of time, although the physiological parameter is typically a distinct parameter derived from one or more measurement channels, such as heart rate derived from one or more ECG channel signals or a $SpO_2$ value derived from one or more plethysmographic channel signals. In an embodiment, the physiological parameters may include heart rate, heart rate variability, ST segment measurements, respiration rate, pulse rate, oxygen saturation, systolic, diastolic and/or mean blood pressure, entropy, sedation and the like.

The physiological channel signals 14 acquired from the subject 12 are supplied to a control and processing unit 16 through a pre-processing stage (not shown) comprising typically an input amplifier and a filter, for example. The control and processing unit 16 converts the signals into digitized format for each measurement channel. The digitized signal data may then be stored in the memory 18 of the control and processing unit 16. In an embodiment, the digitized signal data is utilized by parameter algorithms 20 adapted to record, when executed by the control and processing unit 16, the time series of the physiological parameters to be monitored. The obtained time series of the physiological parameters may be stored in the memory 18. Moreover, the parameter algorithms 20 of the control and processing unit 16 process the digitized signal data and measurements to identify past, current or future occurrence of physiological events.

Generally, each physiological parameter may be assigned one or more alarm limits and/or pattern or condition limit to alert the nursing staff when the parameter reaches or crosses the alarm limit and/or a certain pattern of physiological activity is detected or sensed. For example, a physiological parameter, such as heart rate, may be assigned multiple alarm levels of increasing priority/severity and alarm escalation may be used to escalate a low level alarm to the next level of priority/severity, if the low level alarm persists and/or goes unacknowledged long enough. In an embodiment, the control and processing unit 16 includes an alarm generator for notifying a clinical user with an appropriate alarm signal when a monitored parameter reaches or exceeds the preset alarm limit for such parameter.

In particular, in an embodiment, the control and processing unit 16 uses a signal monitoring algorithm 22 to monitor the successive values of the parameter and to detect events and to generate alarms based on the parameter values. This typically involves comparison of the parameter values with at least one alarm limit stored in memory 18 to detect whether an alarm is to be raised. When a crossing of an alarm limit is detected, the control and processing unit 16 may inform the clinician of the alarm.

In addition to identifying past, current and future occurrences of physiological events, the control and processing unit 16 of the system 10 is configured to estimate patient acuity from the digitized physiological signal data and measurements utilizing an acuity estimation algorithm 24. These data and measurements may be the same or different physiological signals and measurements as those that are utilized to detect physiological events. In an embodiment, the acuity estimation algorithm 24 utilizes measured heart rate variability to determine the patient's acuity, as heart rate variability has been shown to correlate to a patient's healthy ability to compensate for physiological disturbances.

In an embodiment, various means for estimating patient acuity may be utilized by the acuity estimation algorithm 24 of the control and processing unit 16. For example, any rule-based scoring systems or commercial available systems known in the art to determine the degree of illness of a patient may be utilized by the control and processing unit 16 to estimate patient acuity, such as Early Warning Score, Modified Early Warning Score and Rothman Index™.

With further reference to FIG. 1, the control and processing unit 16 may include a sensitivity control algorithm 26 which is configured to determine the sensitivity level to be applied to one or more of the parameter values with respect to the detection of physiological events by the system 10 and/or the generation of alarms by the system. In particular, the sensitivity control algorithm is configured to determine the optimal alarm limit or event detection limit for the various parameters being measured, and to adjust such limit within memory 18. In am embodiment, the derivation of the sensitivity level from acuity level may be accomplished utilizing various methods including, but not limited to, empirical, rule based and learning methods.

In an embodiment, the control and processing unit may include a morphology determination and monitoring algorithm 28 to determine and monitor signal morphology. The control and processing unit is further configured to control the display unit(s) 30 of the system. Interaction with users of the apparatus/system may occur through user interface 32.

Figure 2:
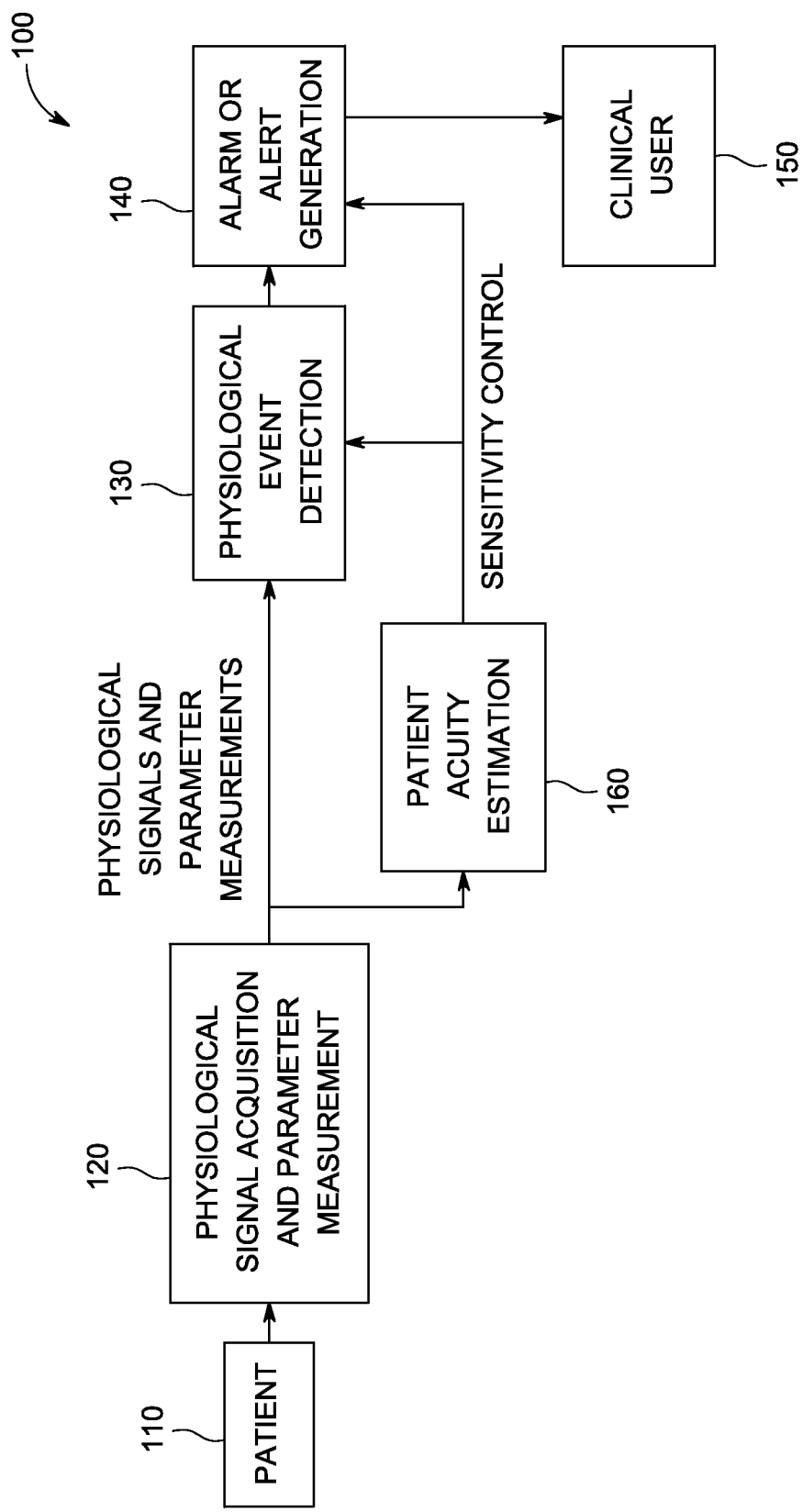
FIG. 2 is a functional block diagram for automatic physiological alarm sensitivity control according to an embodiment of the present invention.

With reference to FIG. 2, an automatic physiological alarm sensitivity control block diagram 100 utilized by the system 10 is illustrated. As discussed above, physiological signals are acquired and parameters are measured from a patient 110 at block 120. These signals and parameters are acquired and measured through the use of various medical devices and apparatuses connected to the patient, as indicated previously. One or more of the physiological signals and parameters and measurements are utilized to detect physiological events and to generate an alarm if the signals and measurements exceed preset levels, a block 130 and 140, respectively. The detection of a physiological event or the generation of an alarm or alert may then be communication to a clinical user at block 150. While the system 10 is operating by continuously or intermittently monitoring a patient, the preset levels for event detection and alarm generation may be adjusted in dependence upon the patient's acuity in real-time. In connection with this, at block 150, one or more of the physiological signals and parameters from block 120 are utilized to estimate patient acuity in real-time. Depending upon the estimated level of patient acuity, the preset levels for event detection and alarm generation stored in memory may be automatically adjusted without requiring input from the clinical user 150. As will be readily appreciated, alarm or event detection threshold levels may be set for one or more of the physiological parameters, including heart rate, heart rate variability, ST segment measurements, respiration rate, pulse rate, oxygen saturation, systolic, diastolic and/or mean blood pressure, entropy, sedation and the like.

For example, if the system 10 estimates that a patient's acuity level has increased relative to a previously determined or estimated acuity level, the sensitivity settings for event detection and alarm generation will be automatically adjusted or updated to make the system more sensitive to signal and measurement changes (i.e., the preset level at which the system detects physiological events and generates alarms will be adjusted). In such case, more alarms may be generated. Likewise, if the system 10 estimates that a patient's acuity level has decreased, the sensitivity settings for event detection and alarm generation will be automatically adjusted or updated to make the system less sensitive to signal measurement changes (i.e., the present level at which the system detects physiological events and generates alarms will be adjusted). In such case, fewer alarms may be generated. In an embodiment, rather than automatically adjusting the present levels for event detection and alarm generation, the system 10 may prompt a clinical user to go ahead and manually adjust the preset levels/limits.

Figure 3:
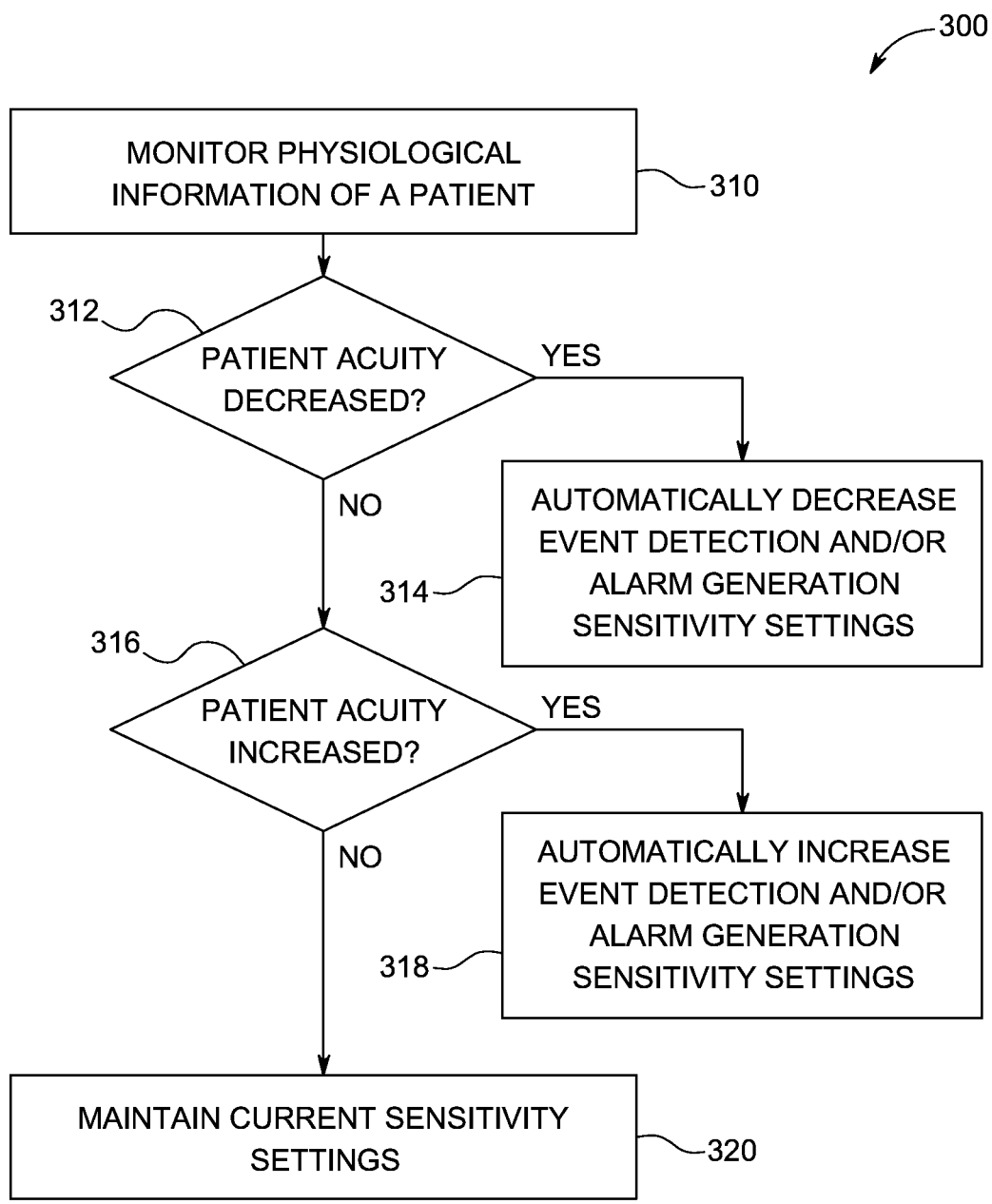
FIG. 3 is a flowchart illustrating a method of physiological monitoring utilizing a patient monitoring system, according to an embodiment of the present invention.

Referring now to FIG. 3, a method 200 of automatically adjusting event detection and alarm generation sensitivity settings of a patient monitoring system. As illustrated therein, at step 310, various devices and apparatuses connected to a patient may monitor physiological information of the patient. As discussed, the physiological information may include Electrocardiogram (ECG), electroencephalogram (EEG), plethysmographic signals, and signals related to blood pressure, temperature, and respiration. These signals and measurements are received by a control unit of the patient monitoring system and are utilized to determine a level of acuity of the patient, at step 312. At step 314, the determined acuity level of the patient is compared to a previously determined acuity level of the patient. If the acuity level has decreased, then the system automatically updates the event detection in alarm sensitivity settings of the monitoring system to decrease system sensitivity, at step 316. If the acuity level has not decreased, the system then determines, at step 318, if the acuity level has increased or has remained the same. If the acuity level has increased, then the system automatically updates the event detection in alarm sensitivity settings of the monitoring system to increase system sensitivity, at step 320. If, however, the acuity level has remained the same, then no changes are made to the sensitivity settings.

As discussed above, in an embodiment, rather than adjusting the sensitivity settings automatically in response to a detected change in patient acuity level, the system may prompt a user to do so when such change in acuity level is detected. As will be readily appreciated, this allows a clinician to manually adjust the sensitivity settings, under prompting from the system, according to his/her personal preferences.

As will be readily appreciated, the present invention allows for optimized physiological alarm system performance of a patient monitoring system. In particular, the system and method of the present invention addresses the problem of alarm fatigue, while also maintaining proper vigilance of acute patients. Moreover, it improves ease of use of patient monitoring systems by eliminating technical controls that clinical users may often ignore.

In an embodiment, a method of adjusting event detection and alarm generation sensitivity settings of a patient monitoring system is provided. The method includes the steps of receiving physiological information from a patient, determining an acuity level of the patient in dependence upon the physiological information received, and automatically updating a sensitivity setting for a system action in dependence upon the determined acuity level of the patient. In an embodiment, the at least one system action includes an alarm generation. In an embodiment, the at least one system action includes an event detection. In an embodiment, the physiological information includes at least one physiological signal, and the method may also include the step of determining at least one physiological parameter from the physiological signals. In an embodiment, the at least one physiological signal includes at least one of ECG, EEG, EMG, blood pressure, respiration, pulse, temperature and plethysmographic signals, and the at least one physiological parameter includes at least one of heart rate, heart rate variability, ST segment measurements, respiration rate, pulse rate, oxygen saturation, systolic blood pressure, diastolic blood pressure, mean blood pressure, entropy and sedation. In an embodiment, the method includes the steps of comparing the determined acuity level to a prior acuity level, increasing the sensitivity setting if the determined acuity level of the patient is less than the prior acuity level, and decreasing the sensitivity setting if the determined acuity level of the patient is greater than the prior acuity level. In an embodiment, the step of determining the acuity level of the patient is carried out utilizing a rule-based scoring system. The rule-based scoring system may be one of Early Warning Score, Modified Early Warning Score and Rothman Index™. In an embodiment, the method may also include the step of generating the alarm when at least one physiological parameter exceeds a sensitivity level setting for such parameter.

In an embodiment, a method of physiological monitoring utilizing a patient monitoring system is provided. The method includes the steps of determining an acuity level of a patient in dependence upon physiological information of the patient, and at least one of automatically updating a sensitivity setting for a system action in dependence upon the determined acuity level of the patient or prompting a user to manually update the sensitivity setting for the system action in dependence upon the determined acuity level. In an embodiment, the step of automatically adjusting one of an event detection sensitivity level and an alarm generation sensitivity level of the patient monitoring system includes adjusting a threshold level for at least of a heart rate, heart rate variability, ST segment measurement, respiration rate, pulse rate, oxygen saturation, systolic blood pressure, diastolic blood pressure, mean blood pressure, entropy and sedation. In an embodiment, the method may include the step of generating an alarm when the threshold level is exceeded. In an embodiment, the patient monitoring system includes a plurality of devices connected to a patient and configured to monitor the physiological information. In an embodiment, the physiological information includes at least one physiological signal, and the method further includes the step of determining at least one physiological parameter from the physiological signals. In an embodiment, the at least one physiological signal includes at least one of ECG, EEG, EMG, blood pressure, respiration, pulse, temperature and plethysmographic signals, and the at least one physiological parameter includes at least one of heart rate, heart rate variability, ST segment measurements, respiration rate, pulse rate, oxygen saturation, systolic blood pressure, diastolic blood pressure, mean blood pressure, entropy and sedation. In an embodiment, the step of determining the acuity level of the patient is carried out utilizing a rule-based scoring system. In an embodiment, the rule-based scoring system is one of Early Warning Score, Modified Early Warning Score and Rothman Index™.

In an embodiment, a system for monitoring a patient is provided. The system includes at least one device connected to the patient and configured to obtain physiological information from the patient, and a control unit electrically connected to the at least one device. In an embodiment, the connection may be a data connection or other communication means known in the art for transferring data or signals. The control unit is configured to determine an acuity level of the patient in dependence upon the physiological information and to automatically adjust one of an event detection sensitivity level and an alarm generation sensitivity level in dependence upon the determined acuity level of the patient. In an embodiment, the physiological information includes at least one physiological signal and the control unit is configured to derive at least one physiological parameter from the physiological signals. In an embodiment, the physiological information utilized to determine the acuity level is the same physiological information utilized to derive the at least one physiological parameter. In an embodiment, the at least one physiological signal includes at least one of ECG, EEG, EMG, blood pressure, respiration, pulse, temperature and plethysmographic signals, and the at least one physiological parameter includes at least one of heart rate, heart rate variability, ST segment measurements, respiration rate, pulse rate, oxygen saturation, systolic blood pressure, diastolic blood pressure, mean blood pressure, entropy and sedation. In an embodiment, the control unit is configured to adjust a threshold level for at least one of the physiological parameters. In an embodiment, the control unit is configured to generate an audible alarm if the threshold level is exceeded. In an embodiment, the system further includes a display unit electrically connected to the control unit.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope.

While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §122, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method of adjusting event detection and/or alarm generation sensitivity settings of a patient monitoring system, comprising the steps of:
   receiving physiological information from a patient, the physiological information including a plurality of physiological signals representing a plurality of physiological parameters;
   determining an acuity level of the patient by monitoring a first physiological parameter of the plurality of physiological parameters; and
   automatically updating a sensitivity setting for a system action for a second physiological parameter in dependence upon the determined acuity level of the patient, the sensitivity setting defining a threshold level at which the system action is initiated;
   wherein the first physiological parameter is different from the second physiological parameter.

2. The method according to claim 1, wherein:
   the at least one system action includes an alarm generation.

3. The method according to claim 2, wherein:
   the at least one system action includes an event detection.

4. The method according to claim 1, wherein:
   the at least one physiological signal includes at least one of ECG, EEG, EMG, blood pressure, respiration, pulse, temperature and plethysmographic signals; and
   the at least one physiological parameter includes at least one of heart rate, heart rate variability, ST segment measurements, respiration rate, pulse rate, oxygen saturation, systolic blood pressure, diastolic blood pressure, mean blood pressure, entropy and sedation.

5. The method according to claim 1, further comprising the steps of:
   comparing the determined acuity level to a prior acuity level;
   decreasing the sensitivity setting if the determined acuity level of the patient is less than the prior acuity level; and
   increasing the sensitivity setting if the determined acuity level of the patient is greater than the prior acuity level.

6. The method according to claim 1, wherein:
the step of determining the acuity level of the patient is carried out utilizing a rule-based scoring system.

7. The method according to claim 6, wherein:
the rule-based scoring system is one of Early Warning Score, Modified Early Warning Score and Rothman Index™.

8. The method according to claim 6, further comprising the step of:
generating the alarm when at least one physiological parameter exceeds a sensitivity level setting for such parameter.

9. The system according to claim 1, wherein:
the first physiological parameter of the plurality of physiological parameters from which the acuity level is determined functions as a global parameter on the basis of which sensitivity settings for a system action for a plurality of other physiological parameters are automatically updated.

10. A method of physiological monitoring utilizing a patient monitoring system, comprising the steps of:
determining an acuity level of a patient in dependence upon a first physiological parameter of the patient; and
automatically adjusting one of an event detection sensitivity level and an alarm generation sensitivity level for a second physiological parameter of the patient in dependence upon the determined acuity level of the patient;
wherein the first physiological parameter is different from the second physiological parameter.

11. The method according to claim 10, wherein:
the first physiological parameter is a heart rate variability of the patient; and
the step of automatically adjusting one of an event detection sensitivity level and an alarm generation sensitivity level of the patient monitoring system includes adjusting a threshold level for the second physiological parameter;
wherein the second physiological parameter includes at least one of a heart rate, ST segment measurement, respiration rate, pulse rate, oxygen saturation, systolic blood pressure, diastolic blood pressure, mean blood pressure, entropy and sedation.

12. The method according to claim 11, further comprising the step of:
generating an alarm when the threshold level is exceeded.

13. The method according to claim 12, wherein:
the method further includes the step of determining values for the first and second physiological parameters from physiological signals received from the patient.

14. The method according to claim 10, wherein:
the patient monitoring system includes a plurality of devices connected to a patient and configured to monitor the physiological parameters.

15. The method according to claim 14, wherein:
the physiological signals include at least one of ECG, EEG, EMG, blood pressure, respiration, pulse, temperature and plethysmographic signals.

16. The method according to claim 10, wherein:
the step of determining the acuity level of the patient is carried out utilizing a rule-based scoring system.

17. The method according to claim 16, wherein:
the rule-based scoring system is one of Early Warning Score, Modified Early Warning Score and Rothman Index.

18. A system for monitoring a patient, comprising:
at least one device connected to the patient and configured to obtain values for first and second physiological parameters of the patient; and
a control unit electrically connected to the at least one device and configured to determine an acuity level of the patient in dependence upon the first physiological parameter, the control unit being further configured to automatically adjust one of an event detection sensitivity level and an alarm generation sensitivity level for the second physiological parameter in dependence upon the determined acuity level of the patient;
wherein the first physiological parameter is different from the second physiological parameter; and
wherein the first physiological parameter is a heart rate variability.

19. The system of claim 18, wherein:
the control unit is configured to derive the physiological parameters from physiological signals received from the patient.

20. The system of claim 19, wherein:
the physiological signals includes at least one of ECG, EEG, EMG, blood pressure, respiration, pulse, temperature and plethysmographic signals; and
the second physiological parameter includes at least one of heart rate, ST segment measurements, respiration rate, pulse rate, oxygen saturation, systolic blood pressure, diastolic blood pressure, mean blood pressure, entropy and sedation.

21. The system of claim 20, wherein:
the control unit is configured to adjust a threshold level for the second physiological parameter.

22. The system of claim 21, wherein:
the control unit is configured to generate an audible alarm if the threshold level is exceeded.

23. The system of claim 18, further comprising:
a display unit electrically connected to the control unit.

* * * * *